United States Patent
Frank

(10) Patent No.: US 6,936,288 B2
(45) Date of Patent: Aug. 30, 2005

(54) METHOD AND COMPOSITION FOR THE TREATMENT OF SHINGLES AND RELATED AFFLICTIONS

(75) Inventor: Steven R. Frank, Golden, CO (US)

(73) Assignee: Klearsen Corporation, Boulder, CO (US)

( * ) Notice: Subject to any disclaimer, the term of this patent is extended or adjusted under 35 U.S.C. 154(b) by 0 days.

(21) Appl. No.: 10/457,376

(22) Filed: Jun. 10, 2003

(65) Prior Publication Data

US 2004/0253325 A1 Dec. 16, 2004

(51) Int. Cl.⁷ .......................... A61K 35/78; A61K 38/00
(52) U.S. Cl. .......................... 424/777; 424/725; 514/2; 514/887
(58) Field of Search .................. 424/725, 777; 514/2, 887

(56) References Cited

U.S. PATENT DOCUMENTS

| | | | |
|---|---|---|---|
| 4,742,046 A | | 5/1988 | Bliah |
| 5,252,330 A | * | 10/1993 | Lee et al. .................. 424/777 |
| 5,482,698 A | | 1/1996 | Griffiths |
| 5,525,338 A | | 6/1996 | Goldenberg |
| 5,919,457 A | | 7/1999 | Uckun |
| 5,945,106 A | * | 8/1999 | Sinnott ..................... 424/774 |
| 6,063,758 A | * | 5/2000 | Lappi et al. .................. 514/2 |
| 6,146,628 A | | 11/2000 | Uckun et al. |
| 6,221,355 B1 | | 4/2001 | Dowdy |
| 6,372,217 B1 | | 4/2002 | Uckun |
| 6,482,805 B2 | | 11/2002 | Uckun et al. |
| 6,492,498 B1 | | 12/2002 | Vallera et al. |
| 2002/0001600 A1 | | 1/2002 | Oldham et al. |
| 2002/0116737 A1 | * | 8/2002 | Thomas et al. ............. 800/288 |
| 2003/0054000 A1 | | 3/2003 | Dowdy |
| 2003/0054377 A1 | | 3/2003 | Rosen et al. |

FOREIGN PATENT DOCUMENTS

| | | | |
|---|---|---|---|
| RO | 87644 A | * | 9/1985 |
| WO | WO-3007972 A | * | 1/2003 |
| ZA | 20000857 A | * | 2/2000 |

OTHER PUBLICATIONS

Nillson et al. Vaxtskyddsnotiser. 1990. vol. 53, No. 4, pp. 104–105, BIOSIS Abstract.*

Popescu et al. Arch. Roumaines de Patholog. Exp. Microbiol. 1988. vol. 47, No. 1, pp. 37–41.*

Pezzuto et al. Toxicol. Let. 1984. vol. 22, No. 1, pp. 15–20.*

Peirce, A. The American Pharmaceutical Association—Practical Guide to Natural Medicines. Williman Morrow and Co. Inc. NY, NY. 1999. pp. 511–513.*

* cited by examiner

*Primary Examiner*—Christopher R. Tate
(74) *Attorney, Agent, or Firm*—Welsh & Flaxman LLC

(57) ABSTRACT

A method and composition for treating herpes zoster varicella and related afflictions is provided. The method is achieved by diagnosing an individual affected with the herpes varicella zoster virus or related afflictions and applying a medicine to the affected area. The medicine comprises anti-viral proteins of a pokeweed plant.

7 Claims, No Drawings

METHOD AND COMPOSITION FOR THE TREATMENT OF SHINGLES AND RELATED AFFLICTIONS

BACKGROUND OF THE INVENTION

1. Field of the Invention

The invention relates to a method and composition for treating Herpes Zoster Varicella ("shingles") and the consequential Postherpetic Neuralgia (PHN). More particularly, the invention relates the treatment of shingles and PHN with anti-viral proteins extracted from pokeweed plants.

2. Description of the Prior Art

In the United States alone, Herpes Zoster Varicella, that is, shingles, affects about 1 million people each year with new cases. Even after the initial infection has been treated, the lingering pain and nerve dysfunction (Post Herpetic Neuralgia—) PHN continues to disturb millions of affected individuals for years. In fact, PHN can be so severe and last for so many years that it is considered a significant factor in suicide for sufferers.

The Varicella Zoster virus, as it manifests itself in shingles, is thought by many to be a re-expression of the childhood disease chickenpox. It has some strong similarities to chickenpox, such as, the appearance of the lesions and the usually once-per-lifetime emergence of the disease. However, there are differences as well. Shingles is caused by the Varicella Zoster virus emerging from dormancy, where it inhabits the nerve ganglion and travels out along the nerve cells until it reaches the skin. Once at the skin, it imbeds itself within the DNA of the skin cells and forces replication. This causes the virus to be replicated. One key difference between chickenpox and shingles is that during the process of nerve migration and replication of the shingles virus, the myelin sheaths of the nerves themselves are damaged when shingles strikes an individual. This damage leaves the sufferer with a highly disturbing sense of tingling along the nerve. In some cases, the damage causes unbearable pain.

People have studied whether shortening the duration of a shingles outbreak leads to a recovery involving less PHN (although there is no known mechanism for consistently shortening the duration). However, any potential correlation has been poorly demonstrated at best.

Shingles is generally accepted as being a viral infection. Current teachings suggest treatment by the administration of an oral anti-viral. At present, the most popular systemic antiviral seems to come from the Acyclovir family or Pencyclovir family. Drugs from these derivatives, when supported with a mechanism to aid in systemic transfer through the digestive system, are intended to reduce the activity and replication of virus throughout the body.

The clinical data shows remarkably poor efficacy when this drug therapy is initiated more than 48 hours after initial symptoms are recognized. When the drug therapy is implemented within the first 48 hours, the response tends to be inconsistent and may offer good results in some subjects and very poor results in other subjects. The treatment process is further complicated as only a small percentage of the cases are identified and treated within the first 48 hours of the onset of symptoms.

Potent systemic anti-virals, such as those of the Acyclovir, Pencyclovir or Famcyclovir families, are only given for a short period of time since long-term administration of the cyclovir derivatives has been associated with renal damage. Additionally, there is no efficacy shown in continued administration beyond 7 days for Famcyclovir (FAMVIR), nor has any efficacy been established for occular involved (opthalmic) zoster.

Unfortunately, a shingles out-break typically endures for 4 to 6 weeks. After this time there is a significant period of healing to repair the damage done to the skin tissues. Even after this period of healing passes, subsequent PHN can last for months to years. Clearly, a short course of anti-virals that doesn't sufficiently quell the outbreak is not an acceptable solution.

Recently, the anti-viral capability of Phytolacca Americana has been recognized. The anti-inflammatory and analgesic qualities of Chaparral (larrea tridentata) have long been acknowledged. Chaparral has been recently shown to be anti-viral and specifically to have efficacy relating to the suppression of Herpes virus replication. Comfrey (symphytum officinale) has long been recognized as a cell proliferator and useful in repairing damaged tissue. Pharmaceutical companies are currently developing derivatives intended for systemic oral and intravenous delivery. While this may be appropriate for the suppression of a systemic viral disease such as AIDS, shingles tends to appear in patches constrained to a relatively small region of the body. Additionally, the virus performs its replication close to the surface of the skin. Consequently, it is the inventor's opinion that the application of systemic anti-virals, such as FAMVIR, causes undue harm by exposing the entire subject's system to the relatively toxic effects that most anti-virals have upon normal organs.

Post Herpetic Neuralgia is pain along the involved nerve, considered by most to be due to the myelin sheath damage that occurred during the initial outbreak. It is the inventor's contention that some of the virus continue to thrive in the Schwann cells which comprise the sheath even after the majority have gone dormant. These remaining virus continue to keep the sheath from being properly repaired and thus extend the period of neuralgia. Since theses cells are not readily accessed by the immune system, continued therapy with systemic anti-viral drugs would be ineffective. The topically applied anti-viral salve described in this patent would diffuse through the tissue and permeate the cells of the nerve sheath killing the virus without immune system support. This is a significant advantage in the treatment of PHN.

A need, therefore, exists for a treatment capable of attacking shingles in an effective manner. The need also exists for a treatment capable of mitigating the adverse conditions following the initial outbreak of shingles, such as, Postherpetic Neuralgia. The present invention provides a method and composition for treating shingles and Postherpetic Neuralgia.

SUMMARY OF THE INVENTION

It is, therefore, an object of the present invention to provide a method for treating herpes zoster varicella and related afflictions. The method is achieved by diagnosing an individual affected with the herpes varicella zoster virus or related afflictions and applying a medicine to the affected area. The medicine comprises anti-viral proteins of a pokeweed plant.

It is also an object of the present invention to provide a method wherein the medicine is in the form of a gel.

It is another object of the present invention to provide a method wherein the gel is formed with xanthan gum.

It is a further object of the present invention to provide a method wherein the medicine includes a symphytom officinale.

It is also another object of the present invention to provide a method wherein the medicine includes larrea tridentate.

It is still another object of the present invention to provide a method wherein the medicine includes sodium benzoate.

It is yet a further object of the present invention to provide a method wherein the medicine includes ascorbic acid.

It is also an object of the present invention to provide a method wherein the anti-viral proteins are extracted from berries of the pokeweed plant.

It is another object of the present invention to provide a method wherein the step of applying includes topically applying the medicine to the affected area.

It is a further object of the present invention to provide a method wherein the related afflictions include Postherpetic Neuralgia.

It is still another object of the present invention to provide a composition for treating herpes zoster varicella and related afflictions. The composition is composed of anti-viral proteins of a pokeweed plant and a delivery agent.

Other objects and advantages of the present invention will become apparent from the following detailed description when viewed in conjunction with the accompanying drawings, which set forth certain embodiments of the invention.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

A method for treating Herpes Zoster Varicella ("shingles") and related afflictions (for example, PHN) is disclosed. In its most basic form, the method is achieved by first diagnosing an individual affected with shingles and subsequently applying a medicine to the affected area, the medicine comprising anti-viral proteins of a pokeweed plant.

Shingles causes a painful rash and is generally identified by symptoms including a rash that develops around the body in a pattern that looks like a belt or band. The band-like rash generally appears on only one side of the body. It is further possible to develop more than one band-like rash as shingles develops. Unlike chickenpox, the rash caused by shingles is normally more painful than itchy.

The period before the rash appears is called the prodromal stage. This is followed by a period of active infection in which a rash of painful blisters is present. Pain may continue for months or even years after the blisters heal. As discussed briefly above, this chronic (long-lasting) pain stage is known as PHN.

In particular, the prodromal stage symptoms include the development of pain, burning, tickling, tingling, or numbness in the area around the affected nerves several days before a rash begins. The discomfort typically occurs on a single side of the body, commonly on the chest, back, abdomen, head, face, neck, or one arm or leg. The prodromal stage symptoms may also include chills, fever, a general feeling of illness, or stomach and intestinal disturbances just before, or along with, the start of the rash. Further prodromal patients may also encounter swelling and tenderness of the lymph nodes.

Once the virus is active, the symptoms includes extreme pain (this pain has been described as "piercing needles in the skin"), a rash consisting of small fluid-filled blisters (fluid within the blister is initially clear, but may become cloudy after 3 to 4 days), and the opening, oozing, and crusting over of the blisters about 5 days after their appearance (these sores will generally heal completely within 2 to 4 weeks).

Once an individual is diagnosed as being infected with shingles, a topical medicine is applied to the affected area. In accordance with a preferred embodiment of the present invention, the medicine is applied in the form of a gel, or other salve, although the medicine may take a variety of forms appropriate for topical application to the skin of an infected individual without departing from the spirit of the present invention.

As briefly mentioned above, the primary effective ingredient of the medicine is the anti-viral proteins of the pokeweed plant. Pokeweed, also called pokeberry or inkberry, is a member of the pokeweed family. It is a tall, simple perennial herb, growing from a thick fleshy root, but reproduces only by seed. Pokeweed is found from Maine to Minnesota and southward, and is fairly common in southern and southeastern Iowa.

Usually, pokeweed grows in rich pasture lands, in recently cleared areas, along fencerows, and in waste places and open spots in woodlands. Pokeweed has a stout, smooth, somewhat purplish stem that is extensively branched and attains a height of 2 to 8 feet. Flowers are borne in elongated clusters (racemes) like chokecherry. The flowers are perfect and regular with four to five sepals that are white or green. The fruit develops into a 10-celled fleshy berry with beautiful crimson juice. The seeds are large, lens shaped, glossy, and black.

Prior to the development of the present treatment technique, most encyclopedias of medicinal plants don't even list pokeweed plants, as the only commonly recognized function they serve is as a purgative. Since diarrhea is not a particularly desirable condition to induce, it's not a very popular herb. Of the few books that list the pokeweed plant and describe its medicinal uses, only the use of the roots and the leaves are advocated. Some books even go so far as to claim the berries are toxic. While virtually anything may be toxic when taken in sufficient quantities, one must ingest quite a bit of pokeweed berries for it to be toxic. In fact, some cultures have actually made pokeberry pies.

In accordance with a preferred embodiment of the present invention, the anti-viral proteins are extracted from the berries of the pokeweed plant for subsequent incorporation in the medicine. The proteins are preferably extracted from the mature berries of the pokeweed plant using a low-heat water extraction process, although other extraction techniques known to those skilled in the art may be utilized without departing from the spirit of the present invention. The low temperature water extraction technique is used so as to not disturb the delicate proteins, acids and other molecules that are the essential purveyors of the medicinal benefits applied in accordance with the present invention.

In accordance with a preferred embodiment of the present invention, the berries are picked in the fall when ripe and stored by freezing until the time at which they are to be processed. The freezing process tends to destroy the cellulose containment of the berry juice and facilitate the extraction process. The berries are simmered with de-ionized water for 5 to 10 minutes. The water is then drained off and retained. New water is added and the process is repeated. After the third boil, all of the valuable proteins have been extracted and the liquid from the three boils is combined.

In addition to the anti-viral proteins of the pokeweed plant, the medicine also includes xanthan gum, symphytom officinale, larrea tridentate, sodium benzoate and ascorbic acid. More specifically, in addition to the pokeweed plant extract, Symphytom Officinale (Comfrey) has been used for ages for it's remarkable ability to facilitate tissue healing. Used in this preparation, it is intended to expedite healing of damaged tissue. In addition, Comfrey is included in the present medicine for it's lesser known anti-inflammatory properties, which function as an effective mechanism in relieving the tingling and pain associated with PHN.

Larrea Tridentata (Chaparral), while it is mostly noted for its support of healthy skin tissue, exhibits a notable analgesic quality that supports the reduction in pain during the PHN and healing phase of Shingles. More recently, Chaparral has been acknowledged as an effective anti-viral agent specifically against herpes virus.

Xanthan gum is a natural gelling agent. The aqueous base of the extracted anti-viral, Comfrey, Chaparral, etc., is gelled with a natural gelling agent (Xanthan Gum) to produce a medium which is readily absorbed by the skin. This is important to facilitate ready access to the dermal layer where the virus is replicating and the damage to tissue is being perpetrated. Ascorbic Acid (Vitamin C) is also added to reduce the pH to about 3 so that the sodium benzoate will be effective as a preservative. The other herbals are included in the water during the simmering of the pokeberries so as to extract the useful ingredients from them as well. The Xanthan gum is added when the product is to be gelled and stored. It is added at 2% weight to volume. In accordance with a preferred embodiment, the ratio is as follows:

2.5 kg of Pokeberries
160 g of Chaparral
80 g of Comfrey
700 g of Ascorbic Acid (un-buffered)
7 liters of deionized water This provides a concentrate from which the gel can be formed. To form the gel, the concentrate is diluted 10:1 with deionized water. Thereafter, the gel is formed through the introduction of 10 g of Xanthan gum to each 500 ml of fluid. The composition is then mixed until smooth. This produces a composition having approximately 2.4% pokeberries by weight.

This resulting medicine is an all-natural topical anti-viral gel that is enormously effective at stopping the proliferation of shingles and reducing the discomfort of Postherpetic Neuralgia. When used on cases of shingles that have already grown to encompass large areas of flesh, it has been demonstrated to stop the progression of the outbreak eliminate the pain and itching and in fact terminate the condition in mere days. Since it is used externally and can be applied for the duration of the outbreak it makes an excellent conjunctive therapy for association with allopathic medicine. In accordance with a preferred embodiment of the present invention, the medicine is applied 4 times daily until the symptoms are gone. Thereafter, application of the medicine is continued for an additional 3 days to ensure that treatment of the virus is complete.

In addition to its usefulness in treating shingles and related afflictions, the present medicine and treatment method may be utilized in the treatment of eczema and female genital herpes.

While the preferred embodiments have been shown and described, it will be understood that there is no intent to limit the invention by such disclosure, but rather, is intended to cover all modifications and alternate constructions falling within the spirit and scope of the invention as defined in the appended claims.

What is claimed is:

1. A method for treating herpes zoster varicella, comprising the following steps:

diagnosing an individual infected with the herpes varicella zoster virus;

applying a medicine to the infected area, the medicine including an extract of a pokeweed berries as its essential active ingredient.

2. The method according to claim 1, wherein the medicine is in the form of a gel.

3. The method according to claim 1, wherein the medicine includes Symphytom officinale.

4. The method according to claim 1, wherein the medicine includes Larrea tridentate.

5. The method according to claim 1, wherein the medicine includes sodium benzoate.

6. The method according to claim 5, wherein the medicine includes ascorbic acid.

7. The method according to claim 1, wherein the step of applying includes topically applying the medicine to the infected area.

* * * * *